(12) United States Patent
Schwab

(10) Patent No.: US 8,177,816 B2
(45) Date of Patent: May 15, 2012

(54) VERTEBRAL ANCHOR

(76) Inventor: Frank J. Schwab, New York, NY (US)

( * ) Notice: Subject to any disclaimer, the term of this patent is extended or adjusted under 35 U.S.C. 154(b) by 743 days.

(21) Appl. No.: 11/850,393

(22) Filed: Sep. 5, 2007

(65) Prior Publication Data

US 2008/0058818 A1    Mar. 6, 2008

Related U.S. Application Data

(60) Provisional application No. 60/842,318, filed on Sep. 5, 2006.

(51) Int. Cl.
*A61B 17/04* (2006.01)
(52) U.S. Cl. ........................ 606/263; 606/246
(58) Field of Classification Search .............. 606/59, 606/60, 246–279, 300–320
See application file for complete search history.

(56) References Cited

U.S. PATENT DOCUMENTS

| | | | | |
|---|---|---|---|---|
| 4,790,303 A | * | 12/1988 | Steffee | 606/300 |
| 4,805,602 A | * | 2/1989 | Puno et al. | 606/267 |
| 6,086,590 A | * | 7/2000 | Margulies et al. | 606/263 |
| 6,325,802 B1 | * | 12/2001 | Frigg | 606/263 |
| 6,802,844 B2 | * | 10/2004 | Ferree | 606/258 |
| 6,811,567 B2 | | 11/2004 | Reiley | |
| 2001/0034522 A1 | * | 10/2001 | Frigg | 606/61 |
| 2002/0040222 A1 | * | 4/2002 | Hashimoto et al. | 606/61 |
| 2002/0055740 A1 | * | 5/2002 | Lieberman | 606/61 |
| 2004/0111088 A1 | * | 6/2004 | Picetti et al. | 606/61 |
| 2005/0267472 A1 | * | 12/2005 | Biedermann et al. | 606/61 |

FOREIGN PATENT DOCUMENTS

FR    2801492 A1 *  6/2001

* cited by examiner

*Primary Examiner* — Eduardo C Robert
*Assistant Examiner* — Lynnsy Schneider
(74) *Attorney, Agent, or Firm* — Senniger Powers LLP

(57) ABSTRACT

An anchor for attaching an elongate member to bone. The anchor includes a base adapted for attaching to bone and a connector mounted on the base. The connector includes a mount for mounting the elongate member and an opening sized and positioned on the connector for receiving a tie for tying the anchor to the bone when the base is attached to the bone.

29 Claims, 4 Drawing Sheets

VERTEBRAL ANCHOR

CROSS-REFERENCE TO RELATED APPLICATIONS

This application claims priority from U.S. Provisional Patent Application No. 60/842,318 filed Sep. 5, 2006, which is hereby incorporated by reference.

BACKGROUND

The present invention is directed to bone anchoring and more particularly to an anchoring method and system for reducing the potential for an anchor to pull out of bone.

Various bone anchors have been developed for mounting structures to bones. For example, rods and/or plates are often attached to vertebrae using anchors such as screws or hooks. In the past, most procedures of this type rigidly held the separate bone elements in fixed positions relative to one another so that over time the bone elements would grow together or fuse. In some instances, metal cables and/or wires were looped around portions of vertebrae and the rods or plates extending between the anchors to securely hold the vertebrae in their respective positions to promote healing and/or fusion.

Sometimes bone is weak and brittle making it difficult to fasten the anchors to the bones. One such example of weak and brittle bones is in patients having osteoporosis. In such instances, screws and hooks may not offer reliable fastening and are prone to failure prior to solid fusion. Further, some surgical techniques do not rigidly fix the bone elements, but allow the bone elements to move a limited distance. This movement can change the loading on the anchors and cause the anchors to pull out of the bone over time. Thus, there is a need for an anchoring system having improved anchoring characteristics and resists pulling out under one or more of these conditions.

BRIEF SUMMARY

The present invention relates to an anchor for attaching an elongate member to bone. The anchor comprises a base adapted for attaching to bone and a connector mounted on the base. The connector includes a mount for mounting the elongate member and an opening sized and positioned on the connector for receiving a tie for tying the anchor to the bone when the base is attached to the bone.

In another aspect, the invention includes an anchor for attaching an elongate member to bone. The anchor comprises a longitudinal shaft having a tip at one end adapted to enter bone and a thread extending along the shaft for advancing the shaft into the bone and holding the shaft in place in the bone. Further, the anchor includes a head mounted on the shaft at a position spaced from the tip. The head has a mount adapted to mount the elongate member to the head and an opening for receiving a tie for tying the anchor to the bone.

In yet another aspect, the invention includes a system for changing alignment of vertebrae of a spinal column. The system comprises an elongate member having a length sufficient to span at least one pair of vertebrae in the spinal column and a plurality of anchors. Each anchor including a connector for connecting the elongate member to the anchor and an opening for receiving a tie for tying the anchor to a vertebra of the spinal column. The system also includes a tie sized for receipt in the opening of the anchor and having a length sufficient to wrap around at least a portion of the vertebra in which one of the anchors is received.

In still another aspect, the invention includes a method of changing alignment of vertebrae of a spinal column. The method comprises mounting a first anchor on a first vertebra and mounting a second anchor on a second vertebra. An elongate member is connected to the first anchor and to the second anchor. At least one of the first and second anchors is tied to the corresponding vertebra.

Other aspects of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
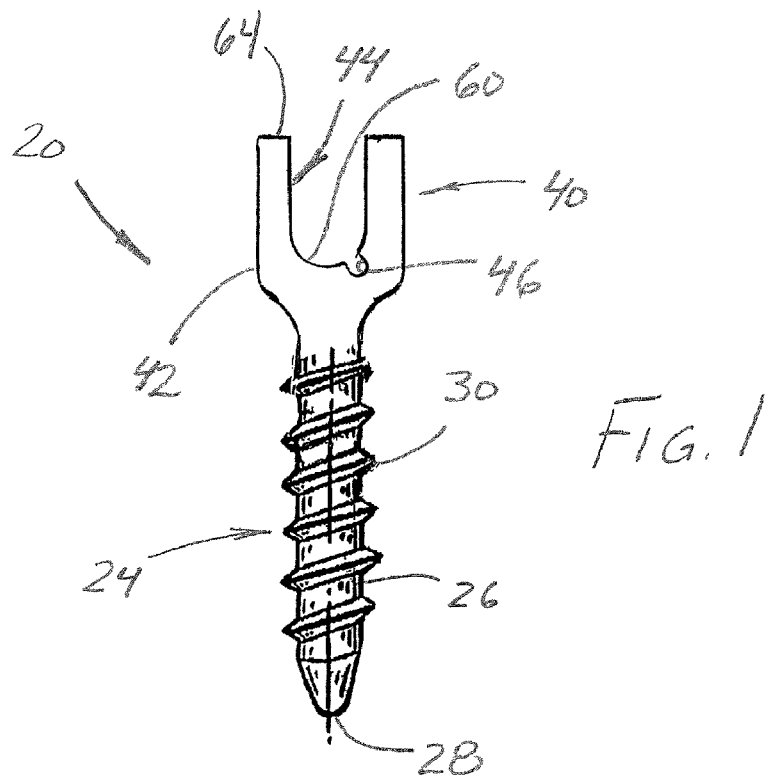
FIG. 1 is a side view of an anchor of a first embodiment of the present invention.

Referring now to the drawings and in particular FIG. 1, an anchor of one embodiment of the present invention is designated in its entirety by the reference number 20. The anchor 20 is intended to attach an elongate member 22 (FIG. 2) to bone (e.g., a pedicle of a vertebra) as will be described in further detail below. As further shown in FIG. 1, the anchor 20 includes a base, generally designated by 24 for attaching the anchor to bone. The base 24 includes a longitudinal shaft 26 having a tip 28 at one end. In one embodiment, the tip 28 has a rounded point for entering bone without inadvertently damaging surrounding bone or tissue. A thread 30 extends along the shaft 26 thereby forming a screw for advancing the shaft into the bone and holding the shaft in place in the bone. A connector, generally designated by 40 is mounted on the base 24. In one embodiment, the connector 40 includes a head 42 mounted on the shaft 26 at a position spaced from the tip 28. The connector 40 includes a mount, generally designated by 44, used to mount the elongate member 22 to the anchor 20. Further, the connector 40 has an opening 46 for receiving a tie 50 (FIG. 2) for tying the anchor 20 to the bone when the base 24 is attached to the bone as will be explained in further detail below.

Figure 2:
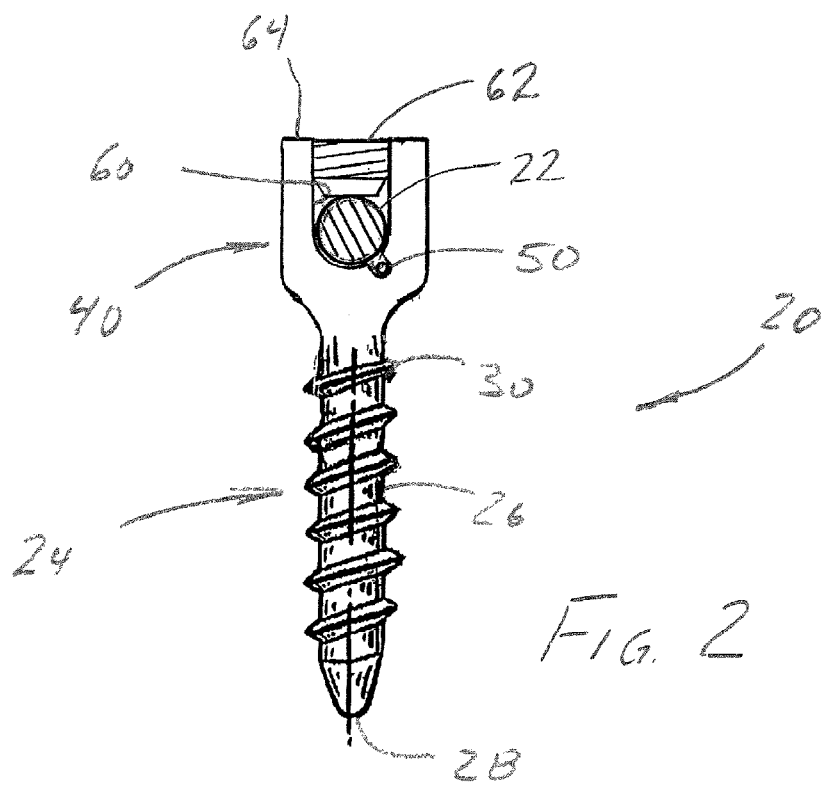
FIG. 2 is a side view of an anchor system including the anchor of FIG. 1.

Although the connector 40 may have other configurations without departing from the scope of the present invention, in one embodiment, the connector includes a U-shaped notch 60 sized and shaped for receiving the elongate member 22. The notch 60 has threads (not shown) extending along each side. The threads engage a threaded fastener 62 as shown in FIG. 2 for holding the elongate member 22 in place. As shown in FIGS. 1 and 2, in the first embodiment of the anchor 20 of the present invention, the opening 46 for receiving the tie 50 extends from a lower surface of the notch 60 spaced from a top surface 64 of the connector 40. As features of this type of connector are well known in the art, they will not be described in further detail. It is contemplated that other types of conventional connectors are also within the scope of the present invention.

Figure 3:
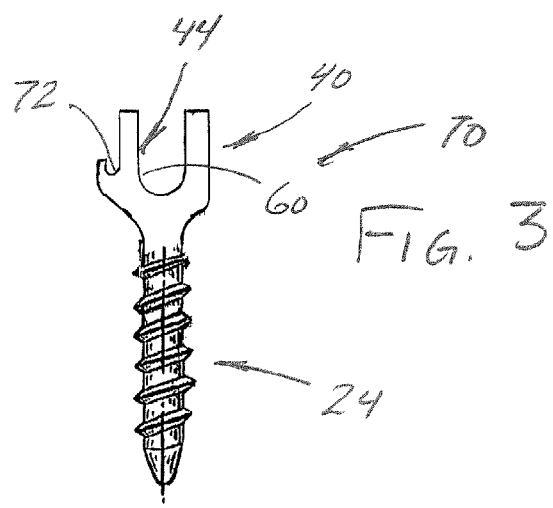
FIG. 3 is a side view of an anchor of a second embodiment.

FIG. 3 illustrates a second embodiment of an anchor of the present invention, generally designated by 70, having an opening 72 for receiving a tie (not shown). The opening 72 of this embodiment comprises a slot positioned beside the mount 44 rather than extending from a lower surface of the mount as in the anchor 20 of the first embodiment. As shown in FIG. 3, the opening 72 of the anchor 70 of the second embodiment is spaced from the notch 60. Because other features of the anchor 70 of the second embodiment are identical to those of the anchor 20 of the first embodiment, they will not be described in further detail. As will be appreciated by those skilled in the art, the anchor 70 of the second embodiment has a configuration which may be advantageous under certain surgical conditions.

Figure 4:
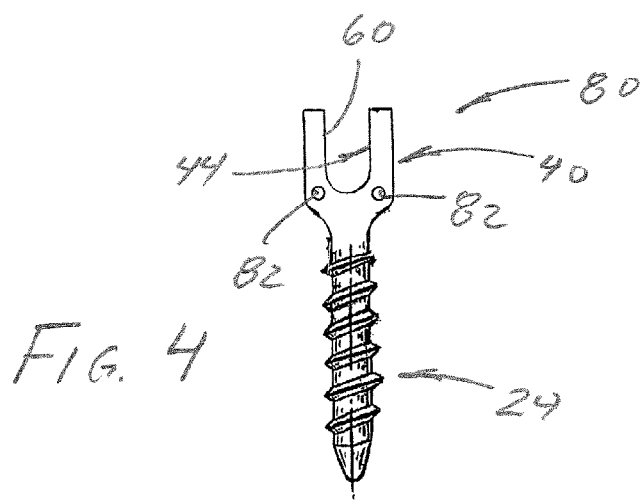
FIG. 4 is a side view of an anchor of a third embodiment.

FIG. 4 illustrates an anchor of a third embodiment of the present invention, generally designated by 80. The anchor 80 of the third embodiment has a pair of openings 82 extending through the head 42. Each of the openings 82 is a hole positioned generally below the mount 44. Each of the openings 82 of the anchor 80 of the third embodiment is spaced from the notch 60. Because other features of the anchor 80 of the third embodiment are identical the previously described anchors, they will not be described in further detail. As will be appreciated by those skilled in the art, the anchor 80 of the third embodiment has a configuration which may be advantageous under certain surgical conditions.

Figure 5:
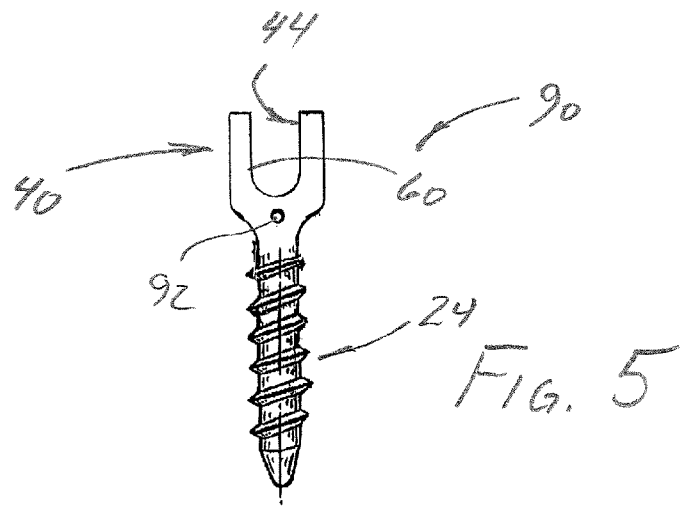
FIG. 5 is a side view of an anchor of a fourth embodiment.

FIG. 5 illustrates a fourth embodiment of an anchor of the present invention, generally designated by 90, having an opening 92 for receiving a tie (not shown) positioned below the mount 44 rather than extending from a lower surface of the mount as in the anchor 20 of the first embodiment. As shown in FIG. 5, the opening 92 of the anchor 90 of the fourth embodiment is a hole spaced from the notch 60 similar to the openings 82 of the anchor 80 of the third embodiment. Because other features of the anchor 90 of the fourth embodiment are identical to those of the anchor 20 of the first embodiment, they will not be described in further detail. As will be appreciated by those skilled in the art, the anchor 90 of the fourth embodiment has a configuration which may be advantageous under certain surgical conditions.

In each of the embodiments described above, the openings are sized and shaped for receiving a tie. Further, the openings extend parallel to the bottom of the notch 60. In alternative embodiments, it is envisioned that the openings may be oblique relative to the bottom of the notch 60. Although some embodiments have been shown, any combination of openings and connectors may be used on the bone anchor without departing from the scope of the present invention.

Figure 6:
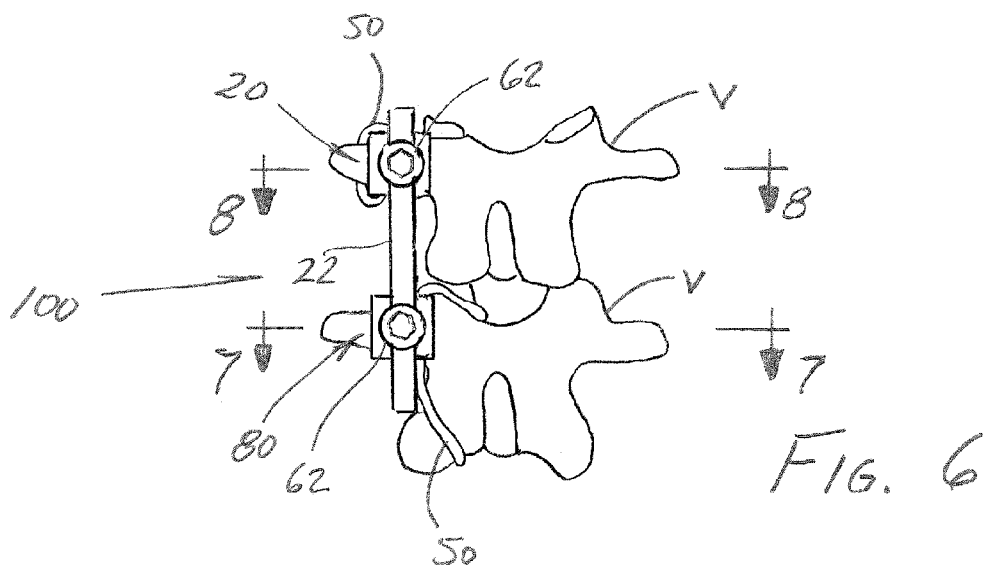
FIG. 6 is a rear elevation of vertebrae having anchors of the first and second embodiments installed therein.
Figure 7:
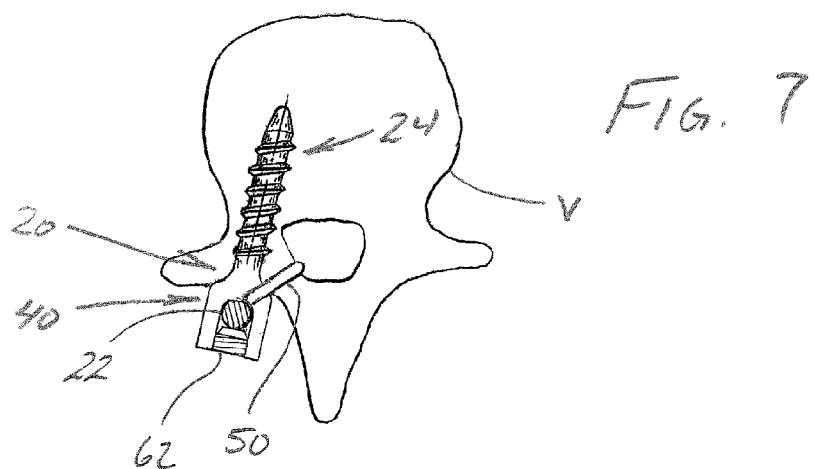
FIG. 7 is a partial section view taken along line 7-7 of FIG. 6.
Figure 8:
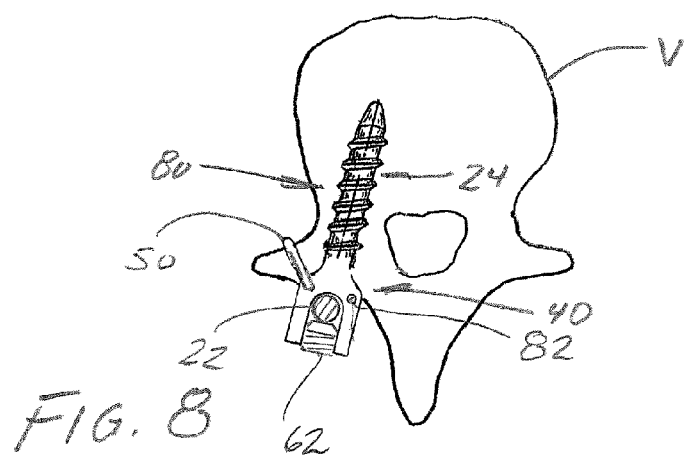
FIG. 8 is a partial section view taken along line 8-8 of FIG. 6.
Figure 9:
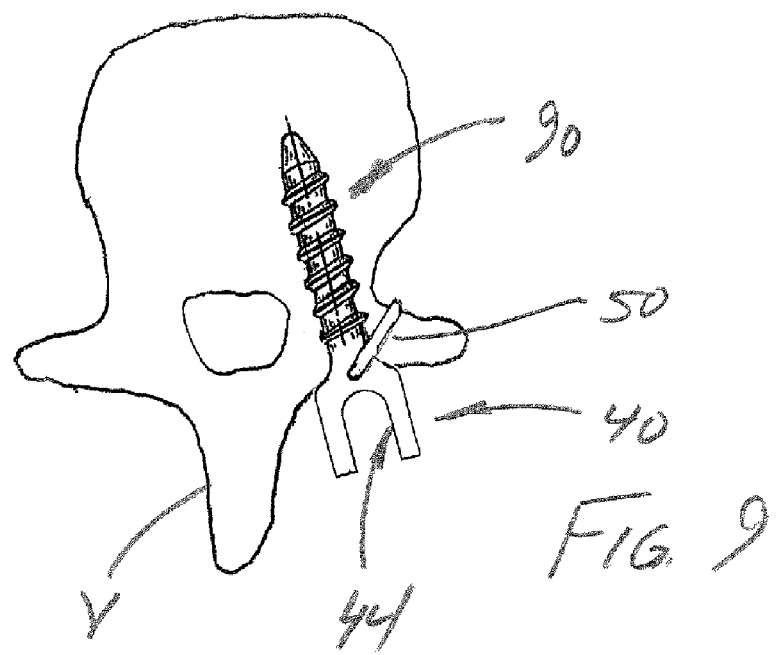
FIG. 9 is a partial section view of a vertebra having an anchor of the fourth embodiment installed.
Figure 10:
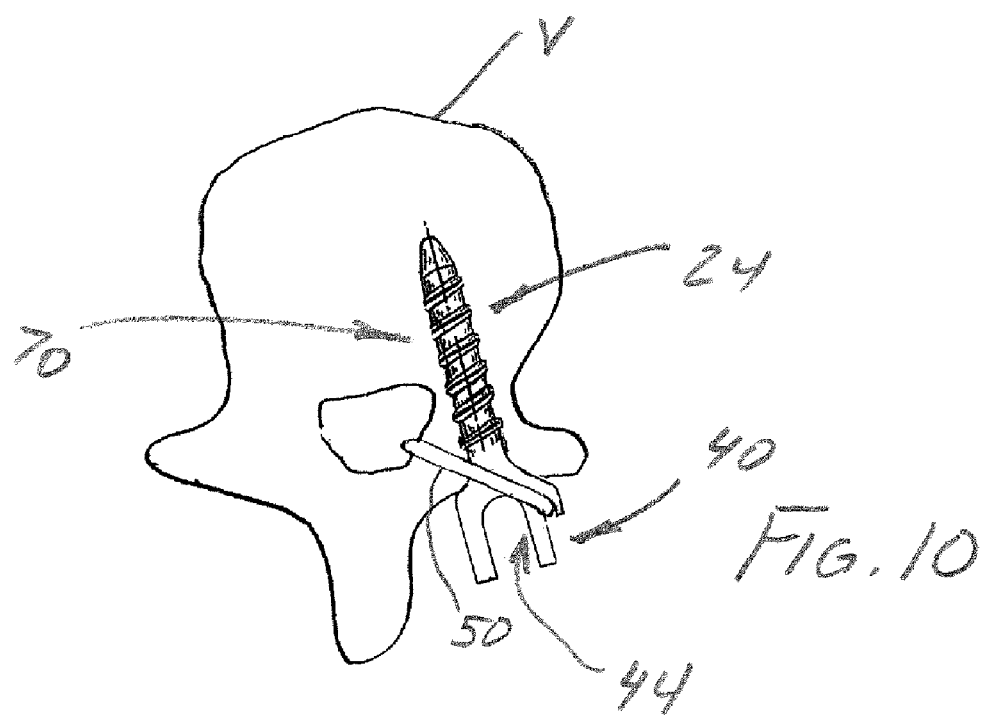
FIG. 10 is a partial section view of a vertebra having an anchor of the second embodiment installed.

In one embodiment shown in FIG. 6, anchors (e.g., anchors 20 and 80) are used in combination with an elongate member 22 and ties 50 to form a system, generally designated by 100, for changing alignment of vertebrae V of a spinal column. As will be appreciated by those skilled in the art, the elongate member 22 may have a variety of lengths. In one embodiment, the elongate member 22 has a length sufficient to span at least one pair of vertebrae in the spinal column as shown in FIG. 6. In some embodiments, the elongate member 22 comprises a rigid member such as a rod, a bar or a plate. In other embodiments, the elongate member 22 comprises a flexible member such as a cable, a wire or a band. The system 100 includes multiple anchors. Each anchor may comprise one the anchors described above. For example, the system 100 shown in FIG. 6 includes an anchor 20 of a first embodiment as seen in FIG. 7 and an anchor 80 of a third embodiment as shown seen in FIG. 8. Alternatively, the system may include an anchor 90 of the fourth embodiment as shown in FIG. 9 or an anchor 70 of the second embodiment. Each anchor includes a connector 40 for connecting the elongate member 22 to the anchor and one or more openings for receiving ties 50 for tying the anchor to a vertebra V of the spinal column. The openings may be one of the openings described above with respect to the anchors of embodiments one through four. In one embodiment, the tie 50 is sized for receipt in the opening of the anchor and has a length sufficient to wrap around at least a portion of the vertebra V in which the respective anchor is received. Although the ties may have other configurations without departing from the scope of the present invention, in some embodiments the ties comprises a cable, a wire, a strap and/or a band. Each of the components of the system 100 may be made of on or more biocompatible materials having suitable strength. Such materials include metal, metal alloys, plastics, carbon-carbon and other composites, ceramics, PEEK, woven or braided polymers and synthetic fibers.

The system 100 described above may be used in a variety of ways which will be readily understood and appreciated by those skilled in the art. One method of use is performed to change alignment of vertebrae of a spinal column. A first anchor is mounted on a first vertebra and a second anchor is mounted on a second vertebra (e.g., a vertebra immediately below the first vertebra. An elongate member 22 is connected to both the first and second anchors using conventional methods. Each of the anchors is tied to the corresponding vertebra. The anchors may be tied to the vertebra either before or after the elongate member is connected to the anchors. Any conventional means may be used to fasten the ends of the tie together. For example, a wire clamp may be used. Alternatively, the ends of the wire may be twisted together to fasten the tie in place. Once the tie is fastened in place, the corresponding anchor is less likely to pull out of the vertebra. Thus, the tie acts to augment the strength of the anchor and overcome the deficiencies of prior art systems.

As will be apparent to those skilled in the art, the tie may be wrapped entirely around the vertebra or around only a portion of the vertebra. For example, the tie may be looped around lamina or pedicles of the vertebra or it may be passed through a transverse process.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An anchor for attaching an elongate member to bone, said anchor comprising:

a base adapted for attaching to bone, the base including a longitudinal shaft having a tip adapted to enter bone and a thread extending along the shaft for advancing the shaft into the bone and holding the shaft in position in the bone;

a connector unitarily joined to the base, the connector including a mount which includes a notch having a width and a depth sized for mounting the elongate member on the connector so the elongate member extends in a longitudinal direction of the notch, and a slot extending through the connector from a first open end to a second open end in a direction generally parallel to the longitudinal direction of the notch, said slot having a side extending between the open ends which opens out of the connector, said slot having a width less than the width of the notch sized for receiving a tie and positioned on the connector spaced from the notch for tying the anchor to the bone when the base is attached to the bone; and
a flexible looped tie received in the slot.

2. An anchor as set forth in claim 1 wherein:
the connector has a top surface facing away from the base; and
the slot is positioned beside the mount.

3. An anchor as set forth in claim 1 wherein the slot is positioned in a side of the connector.

4. An anchor as set forth in claim 1 wherein the tie comprises at least one tie selected from a group of ties consisting of a cable, a wire, a strap and a band.

5. An anchor as set forth in claim 1 in combination with the elongate member.

6. An anchor as set forth in claim 5 wherein the elongate member comprises a rigid elongate member.

7. An anchor as set forth in claim 5 wherein the elongate member comprises a flexible elongate member.

8. An anchor as set forth in claim 7 wherein the flexible elongate member is received in the notch.

9. An anchor as set forth in claim 1 in combination with a fastener for securing the elongate member in the notch.

10. An anchor as set forth in claim 1 wherein the side of the slot opens out of the connector in a direction generally perpendicular to the longitudinal direction of the notch.

11. An anchor for attaching an elongate member to bone, said anchor comprising:
a longitudinal shaft having a tip at one end adapted to enter bone and a thread extending along the shaft for advancing the shaft into the bone and holding the shaft in place in the bone; and
a head mounted on the shaft at a position spaced from the tip, said head having a mount including a notch having a width adapted to mount said elongate member to the head, and a slot extending from the notch having a width less than the width of the notch the slot receiving a looped tie for tying the anchor to the bone, the notch including threads for receiving a threaded fastener in a position that the fastener is at least partially in the notch and engages the elongate member to secure the elongate member to the mount.

12. An anchor as set forth in claim 11 wherein:
the head has a top surface facing away from the shaft; and
the slot is positioned below the mount.

13. An anchor as set forth in claim 11 wherein the tie comprises at least one tie selected from a group of ties consisting of a cable, a wire, a strap and a band.

14. An anchor as set forth in claim 11 in combination with the elongate member.

15. An anchor as set forth in claim 14 wherein the elongate member comprises a rigid elongate member.

16. An anchor as set forth in claim 14 wherein the elongate member comprises a flexible elongate member.

17. An anchor as set forth in claim 11 in combination with said threaded fastener.

18. A system for changing alignment of vertebrae of a spinal column, said system comprising:
an elongate member having a length sufficient to span at least one pair of vertebrae in the spinal column;
a plurality of anchors, each anchor including:
a base adapted for attaching to a respective vertebra of the spinal column;
a connector including a notch having a width sized for receiving the elongate member for connecting the elongate member to the anchor, and an opening for receiving a tie for tying the anchor to the vertebra of the spinal column;
a fastener selectively engageable with the connector and the elongate member to secure the elongate member to the connector; and
a flexible tie received in the opening of at least one of the anchors, the flexible tie including two ends that are fastened together to form a loop.

19. A system as set forth in claim 18 wherein the base of each of the anchors comprises:
a longitudinal shaft having a tip at one end adapted to enter a vertebra of the spinal column; and
a thread extending along the shaft for advancing the shaft into the vertebra and holding the shaft in place in the vertebra.

20. A system as set forth in claim 18 wherein the elongate member comprises at least one member selected from a group of members consisting of a rod, a bar, a band, a plate, a wire and a cable.

21. A system as set forth in claim 18 wherein the tie comprises at least one tie selected from a group of ties consisting of a cable, a wire, a strap and a band.

22. A system as set forth in claim 18 wherein the fastener includes a thread and the notch includes a thread adapted for receiving the thread of the fastener.

23. A system as set forth in claim 18 wherein the tie is free from contact with the plurality of anchors other than the anchor having the opening in which the tie is received.

24. A system as set forth in claim 23 wherein the elongate member is received in the notches of at least two of the plurality of anchors.

25. An anchor for attaching an elongate member to a bone, said anchor comprising:
a base adapted for attaching to the bone;
a connector connected to the base including a mount which includes a notch having a width and a depth sized for mounting the elongate member on the connector so the elongate member extends in a longitudinal direction of the notch, the connector also including an opening extending through the connector in a direction generally parallel to the longitudinal direction of the notch; and
a flexible tie received in the opening, the flexible tie including two ends that are fastened together to form a loop;
in combination with the elongate member received in the notch.

26. An anchor as set forth in claim 25 wherein the opening includes a slot.

27. An anchor as set forth in claim 25 wherein the opening includes a hole spaced from the notch.

28. An anchor as set forth in claim 25 wherein the opening has a width less than the width of the notch.

29. An anchor as set forth in claim 25 wherein the base includes a longitudinal shaft having a tip at one end adapted to enter bone and a thread extending along the shaft for advancing the shaft into the bone and holding the shaft in position in the bone.

* * * * *